Figure 1:
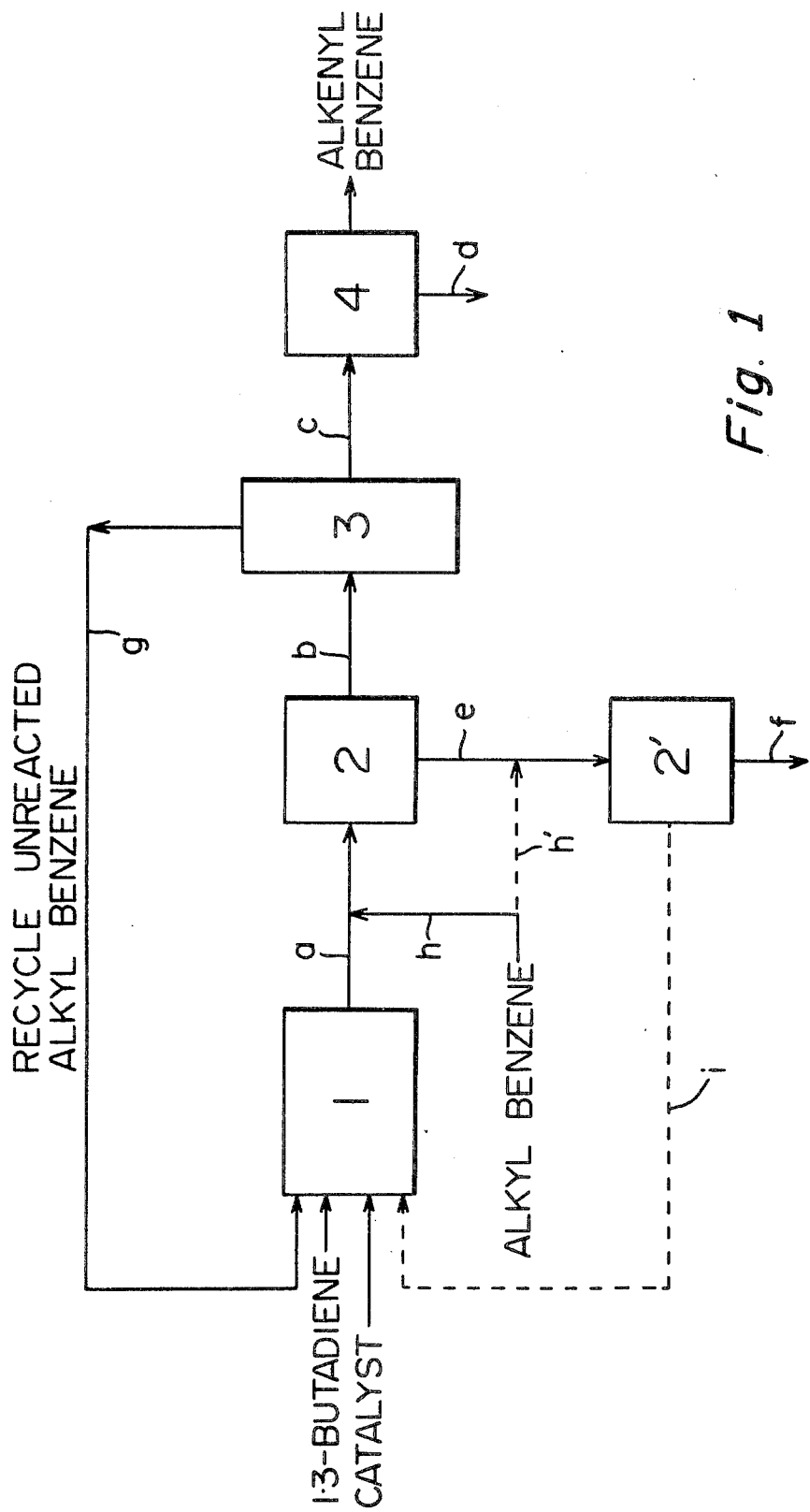

United States Patent [19]

Iwata et al.

[11] 4,018,840

[45] Apr. 19, 1977

[54] PROCESS FOR PREPARING ALKENYLBENZENES

[75] Inventors: Kazumi Iwata; Michiyuki Tokashiki; Takeo Shima, all of Iwakuni, Japan

[73] Assignee: Teijin Limited, Osaka, Japan

[22] Filed: Dec. 24, 1974

[21] Appl. No.: 536,128

[52] U.S. Cl. .............................................. 260/668 B
[51] Int. Cl.$^2$ ........................................ C07C 15/09
[58] Field of Search ................... 260/668 B, 671 A

[56] References Cited

UNITED STATES PATENTS

| 3,223,742 | 12/1965 | Eberhardt | 260/668 B |
| 3,766,288 | 10/1973 | Shima et al. | 260/668 B |
| 3,904,702 | 9/1975 | Mitchell | 260/668 B |

FOREIGN PATENTS OR APPLICATIONS

| 41-16377 | 9/1966 | Japan | 260/668 B |

OTHER PUBLICATIONS

Morton, Lab. Technique in Organic Chemistry, 1st edition, pp. 1 and 9 (1938).

*Primary Examiner*—D. Horwitz
*Attorney, Agent, or Firm*—J. Edward Hess; Donald R. Johnson

[57] ABSTRACT

In the process for preparing alkenylbenzene by the catalytic reaction of alkylbenzenes and 1,3-butadiene in the presence of an alkali metal catalyst, the improvement which comprises effecting the preliminary contact of the freshly fed alkylbenzene with the reaction product of said catalyst reaction and thereafter catalytically reacting said alkylbenzene with said 1,3-butadiene.

4 Claims, 1 Drawing Figure

PROCESS FOR PREPARING ALKENYLBENZENES

This invention relates to an improved process for preparing alkenylbenzenes from alkylbenzenes and 1,3-butadiene advantageously on a commercial scale with improved yields using a curtailed amount of catalyst and by means of a simple operation and apparatus.

More particularly, the invention relates to a process wherein in the process for preparing alkenylbenzenes by the catalytic reaction of alkylbenzenes with 1,3-butadiene in the presence of an alkali metal catalyst the aforementioned catalytic reaction with 1,3-butadiene is carried out after first having contacted the freshly fed alkylbenzene with the above catalytic reaction product.

For instance, as disclosed in U.S. Pat. No. 3,244,758, the preparation of alkenylbenzenes by the catalytic reaction of alkylbenzenes with 1,3-butadiene in the presence of an alkali metal catalyst is known. In this suggested method, expensive metallic potassium must be used in a considerably great amount for obtaining the intended alkenylbenzenes in good yield.

With a viiew to overcoming the foregoing disadvantage of the above known method, we have now found that it is possible to obtain the alkenylbenzenes advantageously with improved yield using a curtailed amount of catalyst as well as a simple operation and apparatus, this being achieved by a process wherein in carrying out the aforesaid reaction the freshly fed alkylbenzene is submitted to the catalytic reaction with the aforesaid 1,3-butadiene after first having been brought into contact with the reaction product of the aforementioned catalytic reaction.

The alkali metal catalysts used in the foregoing catalytic reaction are known to be very sensitive to water and molecular oxygen. Hence, the foregoing catalytic reaction is usually carried out in an atmosphere of a dried inert gas, say, nitrogen and by introducing to the reaction zone reactants that have undergone a dehydration operation. However, while it is not impossible to effect the complete dehydration of the reactants, it is extremely difficult from the practical operations standpoint. Again, it would not be practical from the standpoint of operations and apparatus needed to carry out such a complete dehydration, because it would be extremely complicated and costly.

We found that water in an amount of, say, about 3 ppm and molecular oxygen in an amount of, say, about 2 ppm that usually could be present in the alkylbenzene introduced to the aforesaid catalytic reaction system had an action of impeding the reaction, and that this was of such a magnitude as could not be ignored. It was further found that the presence of these reaction impeding substances was promoting the dimerization of the starting 1,3-butadiene the so formed dimer was difficult to isolate at the time of recovering by distillation the unreacted alkylbenzene contained in the reaction product for recycling and reusing same, with the consequence that it would circulate entrained in the alkylbenzene being reused to accumulate in the recycle system with the continuance of the reaction. The accumulation was of such an amount as could not be ignored to become a cause of impeding the reaction. We also found that the presence of the chain unsaturated hydrocarbons having the carbon-to-carbon triple bond that could be contained in a small amount in the starting alkylbenzene likewise had an adverse effect on the aforesaid catalytic reaction.

As a result of having noted this side reaction impeding effect that resulted from heretofore ignored small amount of water and molecular oxygen on the catalytic reaction of alkylbenzenes and 1,3-butadiene in the presence of an alkali metal catalyst, we found that the aforesaid adverse effect or reaction impeding action could be overcome and an improvement in yield of, say, ca. 5% or more could be achieved by a procedure consisting of not introducing the freshly fed starting alkylbenzene directly to the reaction zone but by introducing said alkylbenzene, say, to an optional point in the reaction system anywhere from that point the reaction product leaves the reaction zone to and inclusive of the zone where the unreacted alkylbenzenes contained in the reaction product is distilled and recovered. Alternatively, the alkylbenzene could be introduced at a point in a line located before the aforesaid distillation and recovery zone, through which line the separated catalyst system containing the catalyst and a small amount of the reaction product stream that have left the catalyst separating zone is flowing, thereby effecting the preliminary contact of said alkylbenzene with the catalytic reaction product. Thereafter the catalytic reaction of the so pretreated starting alkylbenzene could be carried out with 1,3-butadiene in the presence of an alkali metal catalyst.

It was further found that this improvement could be carried out with a simple operation and apparatus in that there was only the necessity of contacting the freshly fed alkylbenzene with the reaction product in advance, with the consequence that the practice of this improvement on a commercial scale was an exceeding simple matter.

It is therefore an object of the present invention to provide a commercially advantageous process for the preparation of alkenylbenzenes from alkylbenzenes and 1,3-butadiene with improved yields using a curtailed amount of catalyst and by means of a simple operation and apparatus.

Other objects and advantages of the present invention will become apparent from the following description.

As the starting alkylbenzenes to be used in the invention process, there can be mentioned the compounds having substituted thereon at least one alkyl radical of 1 or 2 carbon atoms. Examples of such compounds include those having thhe following formula (1):

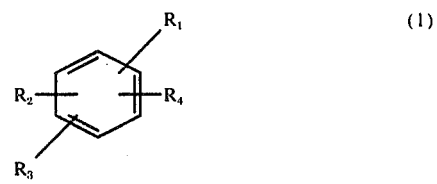

wherein $R_1$ is an alkyl radical of 1 or 2 carbon atoms, and $R_2$, $R_3$, and $R_4$, which may be the same or different, are each hydrogen or an alkyl radical of 1 – 3 carbon atoms. As preferred examples of alkylbenzenes of the above formula (1), included are such as toluene, xylene, ethylbenzene, trimethylbenzene and tetramethylbenzene, especially preferred being o-xylene, m-xylene and p-xylene. These alkylbenzenes can be used either singly or as mixtures of two or more thereof.

The starting alkylbenzene to be freshly fed in the invention process may be one whose content of water and/or oxygen is of an order as has been used heretofore. Usually used is one whose oxygen content does not exceed about 10 ppm, and preferably does not exceed about 5 ppm and/or whose water content does not exceed about 10 ppm, and preferably does not exceed about 5 ppm. Hence, in the invention process, the dehydration and deoxygenation operations of the starting alkylbenzene to be freshly fed need not be conducted in as complicated and strict manner as in the case with the conventional methods. Thus, in this respect also, the invention process is more advantageous for practicing the preparation of alkenylbenzenes on a commercial scale.

While the starting alkylbenzenes to be freshly fed can be used without undergoing any special operations for removing its water and/or oxygen content, preferred are those whose water and/or oxygen content has been reduced in advance to about that indicated hereinabove. As methods of reducing the water content of the starting alkylbenzenes, there can be mentioned, for example, the adsorptive separation method consisting of treating the starting alkylbenzene with such materials as silica gel, molecular sieves and activated alumina, or a method of treatment consisting of contacting the starting alkylbenzenes with a substance which selectively reacts therewith, such, for example, as metallic calcium, calcium oxide and sodium oxide. On the other hand, as methods of reducing the dissolved oxygen, there can be mentioned that of dissipating the oxygen by heat treating, distillation or evaporation or that of contacting the starting alkylbenzene with a substance which selectively reacts with oxygen. The alkylbenzene to be freshly fed to the reaction system is usually fed in an amount corresponding to the amount of alkylbenzene consumed in the catalytic reaction.

On the other hand, 1,3-butadiene, the other starting reactant used in the invention process, may be one prepared by any method. Further, there is imposed no particular restriction as to the purity of the 1,3-butadiene. For instance, crude butadiene obtained by the dehydrogenation of butane or butene can be used as such, or 1,3-butadiene obtained by purifying the foregoing crude butadiene by a method such as extraction can also be used. In the case of 1,3-butadiene, it is preferred to use it in the reaction after dehydration as in the case with the conventional methods. As dehydration methods, there can be mentioned, for example, that of adsorptively separating the water with a suitable adsorbent such as activated alumina, silica gel, molecular sieves and activated charcoal, or that of submitting the 1,3-butadiene to low-temperature processing. While the lower the water content of the starting 1,3-butadiene, the more it is to be preferred, usually preferred is one whose water content is from about 0.1 to about 10 ppm, and more preferably no more than about 5 ppm. On the other hand, the content of oxygen is preferably an amount not exceeding about 5 ppm.

In carrying out the invention process, except that the freshly fed alkylbenzene is catalytically reacted with 1,3-butadiene after first having contacted it with the catalytic reaction product, the reaction conditions are imposed no special restrictions and can be freely chosen.

As the alkali metal catalyst used in the invention process, there can be named, for example, metallic potassium, which may be used alone, or a mixture of metallic potassium and metallic sodium. As known, a mixture of metallic sodium and an inorganic potassium compound, e.g., potassium carbonate, potassium oxide, potassium hydroxide or a potassium halide, which has been heat treated in the absence of oxygen and water can also be used. Also usable is a catalyst obtained by depositing either metallic potassium or a mixture of metallic potassium and metallic sodium on an inorganic carrier such, for example, as potassium oxide, calcium oxide, silicon oxide, silica-alumina and graphite.

While there is imposed no special restriction as to the amount in which the catalyst is used, an amount smaller than in the case of the prior art will suffice. In the case of metallic potassium, it is preferably used in an amount of from about 0.0005 weight part to about 0.4 weight part per 100 weight parts of the alkylbenzene present in the reaction system, while in the case of a mixture of metallic potassium and metallic sodium, the amount used of the former is preferably from about 0.0005 weight part to about 0.4 weight part and the amount used of the latter is preferably an amount not exceeding about 0.5 weight part per 100 weight parts of the alkylbenzene. Especially preferred in the case of metallic potassium is an amount from about 0.001 weight part to about 0.1 weight part, while in the case of a mixture of metallic potassium and metallic sodium especially preferred amounts are from about 0.001 weight part to about 0.1 weight part of the former and from about 0.001 weight part to about 0.1 weight part of the latter, per 100 weight parts of the alkylbenzene present in the reaction system. When using the alkali metal catalyst in such small amounts as indicated above, even the presence of small amounts of water and/or oxygen as well as other reaction impeding substances has extremely adverse effects on the reaction results. Hence, the invention process brings about especially superior improvements when applied to cases such as this where the amount used of the catalyst is curtailed. Needless to say, the effects of preventing the reaction impeding action are also achieved in the case where the catalyst is used in larger amounts.

In the invention process, as hereinbefore indicated, in preparing alkenylbenzenes by the catalytic reaction of the aforementioned alkylbenzenes with the aforementioned 1,3-butadiene in the presence of an alkali metal catalyst such as hereinbefore described, the freshly fed alkylbenzene is first contacted with the reaction product of the foregoing catalytic reaction and thereafter catalytically reacted with the foregoing 1,3-butadiene.

The foregoing reaction product may be the product as obtained from the reaction zone, or it may be the mother liquor resulting after the catalyst has been separated, say, by such means as gravity precipitation, centrifugation or filtration, or it may be the residual liquor resulting after having recovered the unreacted alkylbenzene from said mother liquor by distillation, or it may be the residual liquor that results after the intended alkenylbenzene has been collected from said residual liquor, or it may be the spent catalyst system containing a small quantity of the reaction product containing the aforesaid separated catalyst. Preferably used is the reaction product that is present in the system anywhere from the point of its withdrawal from the reaction zone up to and inclusive of the alkenylbenzene recovery zone as well as the reaction product constituting the aforesaid spent catalyst system.

The contact of the freshly fed alkylbenzene with the reaction product such as above described can be accomplished by merely mixing the two components.

This contact can be achieved by any one of such methods as, for example, that of adding the freshly fed alkylbenzene to the alkali metal catalyst-containing alkenylation reaction product that has left the reaction zone, that of adding the alkylbenzene to the mother liquor containing the intended alkenylbenzene resulting after separation of the solid or liquid alkali metal catalyst from said alkenylation reaction product, that of adding the alkylbenzene to the aforesaid spent catalyst system containing a part of the separated reaction product, or that of adding the alkylbenzene to the residual liquor that results after distilling off the unreacted alkylbenzene or intended alkenylbenzene from the aforesaid reaction product.

This contact pretreatment does not require any special heating or cooling means, the temperature possessed by the reaction product stream that leaves the catalytic reaction zone being usable, i.e., a wide range of temperature from the catalytic reaction temperature to, say, room temperature will do. Usually, a temperature from room temperature to about 250° C. can be used. As the contact time, a time sufficient for the catalytic reaction product and the starting alkylbenzene to become thoroughly mixed will do. Usually, a contact time ranging from about 1 second to about 2 hours can be used.

The apparatus for effecting the contact between the freshly fed alkylbenzene and the aforesaid reaction product may be of any form as long as it is one in which the alkylbenzene and the alkenylation reaction product can be suitably mixed. For example, such apparatus as a stirring tank equipped with a mechanical stirrer and line mixer are used. In carrying out the contact treatment, it is preferably carried out while causing the presence of substantially no oxygen or water in the unfilled space parts of the apparatus. The unfilled space parts are preferably filled with an inert gas such, for example, as dried nitrogen or dried argon, or filled with a vapor of alkylbenzene by carrying out the treatment at a temperature above the boiling point of alkylbenzene. After having contacted the freshly fed alkylbenzene with the reaction, either the alkylbenzene or the catalyst is separated.

The reaction of alkylbenzene and 1,3-butadiene can be carried out in the presence of the hereinbefore-described alkali metal catalysts at a temperature of usually from about 90° to about 250° C., preferably from about 100° to about 220° C., and more preferably from about 110° to about 200° C. The reaction can be carried out at a molar ratio of alkylbenzene to 1,3-butadiene which can be suitable chosen fromm the conventional conditions. For example, a range of alkylbenzene:1,3-butadiene of 1:about 0.001 — about 0.4, preferably 1:about 0.01 — about 0.3, and more preferably 1:about 0.05 — about 0.2 can be used. A reaction time of usually from about 5 minutes to about 10 hours is sufficient, a preferred reaction time being from about 10 minutes to about 8 hours.

Preferred modes of practicing the invention process will be described by reference to FIG. 1. In the FIGURE the reference numeral 1 denotes the catalytic reaction zone where the catalytic reaction between the alkylbenzenes and 1,3-butadiene is carried out in the presence of the alkali metal catalyst; 2 is the catalyst separator for separating the catalyst from the reaction product that has left the catalytic reaction zone; 3 is the unreacted alkylbenzene separator for recovering the unreacted alkylbenzene contained in the reaction product, which separator is usually a distillation column; and 4, which also is usually a distillation column, is the alkenylbenzene separator for separating and collecting the intended alkenylbenzene from the residual liquor remaining after separation of the unreacted alkylbenzene. On the other hand, 2' is the catalyst separator for separating the catalyst from the freshly fed alkylbenzene that was added to the catalyst system leaving the separator 2 and containing a part of the reaction product.

According to the invention process, the freshly fed alkylbenzene is not introduced directly to the catalytic reaction zone 1 but is introduced to the reaction product stream at line $a$ where it has left the reaction zone 1. The alkylbenzene which has been thus contacted with the reaction product is then separated at the catalyst separator 2 from the catalyst which has served its purpose, and the remaining mother liquor is conveyed via line $b$ to the unreacted alkylbenzene separator 3. The unreacted alkylbenzene recovered by distillation at the separator 3 and the freshly fed alkylbenzene that was added at line $a$ are then conveyed together and introduced to the catalytic reaction zone 1 via line $g$, where they are catalytically reacted with 1,3-butadiene.

The residual liquor that has left the alkylbenzene separator 3 is conveyed via line $c$ to the alkenylbenzene separator 4, where the intended alkenylbenzene is collected by distillation. The distillation residue is discharged via line $d$. While it is preferred in the invention process that the freshly fed alkylbenzene be commingled and contacted with the reaction product at between the aforesaid line $a$ and the separator 3, it may also be added to line $c$ or $d$ or, if desired, to the separator 4. The alkylbenzene contacted with the reaction product by addition to line $c$ or $d$ or the separator 4 can then be separated and fed to the reaction zone 1.

In accordance with another mode of the invention process, the alkylbenzene is introduced via line $h'$ shown in broken line in the FIGURE to the catalyst system separated at the catalyst separator 2 and containing a part of the reaction product. In this mode the pretreated freshly fed alkylbenzene can be separated from the catalyst by the provision of another catalyst separator 2', after which the catalyst can be discharged externally of the system via line $f$, while the pretreated freshly fed alkylbenzene can be fed to the catalytic reaction zone 1 via line $i$ similarly shown in broken line. If desired, it is also possible to omit the foregoing catalyst separator 2' and directly feed the pretreated alkylbenzene to said zone 1.

Thus, as described hereinbefore, the intended improvements can be achieved by extremely simple operations and apparatus according to the invention process. While the particulars as to the reaction mechanism by which the effects of preventing the reaction impeding actions are achieved by the invention process are not fully known as yet, the improvement effects can be readily appreciated by a comparison of the results of the hereinafter given examples and control experiments. Modes of practicing the invention process will be more fully illustrated by the following examples and control experiments.

The yield of alkenylbenzene was calculated as follows:

$$\text{Yield (\%)} = \frac{54}{160} \times \frac{\begin{bmatrix}\text{Weight of reaction}\\\text{liquid at reaction}\\\text{outlet (g)}\end{bmatrix} \times \begin{bmatrix}\text{Increase}\\\text{in concentration}\\\text{of alkenylbenzene}\\\text{in reaction zone (wt. \%)}\end{bmatrix}}{[\text{Amount of 1,3-butadiene used (g)}]}$$

EXAMPLE 1 and Control 1

0.13 Part by weight of metallic sodium (0.020 wt. % based on starting o-xylene) and 0.13 part by weight of metallic potassium (0.020 wt. % based on starting o-xylene) were melt blended under a stream of dried nitrogen (oxygen content 1 ppm, water content 0.5 ppm) to prepare an alloy. To the so prepared alloy was then added 650 parts by weight of o-xylene dehydrated in advance with molecular sieves type 4A (oxygen content 5.5 ppm, water content 4.5 ppm). The mixture was then heated for 30 minutes with stirring by raising the inside temperature of the reactor up to 130° C., following which the reaction was carried out by introducing 35 parts by weight of dehydrated 1,3-butadiene over a 2-hour period.

After completion of the reaction, the product was promptly cooled to 110° C., and 10 parts by weight thereof was collected for use as sample for analysis (Control 1). To the reaction product remaining after collection of the foregoing sample for analytic use was added 650 parts by weight of o-xylene of the same grade as that used above, after which the mixture was stirred for 20 minutes at 70° C. The stirring was stopped and the product — o-xylene mixture was left to stand still for 30 minutes while being held at 70° C. to separate the mixture into a catalyst phase and a hydrocarbon liquid phase. This hydrocarbon liquid phase pretreated with the reaction product was distilled at atmospheric pressure while holding it in an atmosphere of dried nitrogen to ensure that it did not contact air or water. 650 Parts by weight of the fraction obtained after collecting 15 parts by weight of the first fraction of distillate was used as the starting material of the second reaction (Example 1 according to the invention process) and reacted with 1,3-butadiene using a catalyst of the same composition as that used in the first reaction (Control 1) and under identical reaction conditions. After completion of the second reaction (Example 1), the reaction product was cooled to room temperature. When it was weighed, it was found to be 695 parts by weight.

When the intended 5-(o-tolyl)pentene-(2) contained in the first and second reaction products was quantitatively analyzed by gas chromatography, the concentration of the first reaction product (Control 1) and 12.6% by weight, while the concentration of the second reaction product (Example 1) was 13.0% by weight. Further, the concentration of the intended product in the o-xylene used as the starting material of the second reaction (Example 1) was below its quantitatively determinable limit (0.02 weight %). The yield of the intended product in the case of Example 1 was 88%, while that of Control 1 was 83%.

EXAMPLE 2 AND CONTROL 2

0.32 Part by weight of metallic sodium (0.050 wt. % based on the starting o-xylene) and 0.060 part by weight of metallic potassium (0.0092 wt. % based on the starting o-xylene) were melt blended under a stream of dried nitrogen (identical specification as that of Example 1) to prepare an alloy. To the so prepared alloy was then added 650 parts by weight of o-xylene dehydrated in advance with molecular sieves type 4A (identical grade as that of Example 1). The mixture was then heated for 30 minutes with stirring by raising the inside temperature of the reactor up to 140° C. The reaction was then carried out by introducing 35 parts by weight of dehydrated 1,3-butadiene over a period of 1.5 hours (first reaction). Simultaneously with the completion of the reaction the stirring was stopped, while maintaining the inside temperature at 140° C. The product was left to stand still for 30 minutes to separate it into a catalyst phase and a liquid phase of the intended product. When the upper layer liquid phase of the intended product was withdrawn and weighed, it was 681 parts by weight (Control 2).

Seven hundred parts by weight of fresh o-xylene was added to the total amount of the catalyst phase (about 4.3 parts by weight) while ensuring that it did not come into contact with air or water, and the preliminary contact treatment with the reaction product was carried out by stirring the mixture for 30 minutes at room temperature, and thereafter the mixture was left to stand still for 60 minutes to separate the catalyst phase and the o-xylene phase. The latter (650 parts by weight) was then transferred to a reactor charged with a catalyst of the same composition and amount as that used in the first reaction, while ensuring that it did not come into contact with air or water, and reacted with 1,3-butadiene under identical conditions as in the first reaction. The product of the second reaction (Example 2) amounted to 686 parts by weight.

When the intended 5-(o-tolyl)pentene-(2) in the starting material and product was quantitatively analyzed, the following results were obtained.

|  | Concentraton of 5-(o-tolyl)pentene-(2) (wt.%) |
| --- | --- |
| First reacton liquid (Control 2) | 12.4 |
| o-xylene used in the second reaction | 0.10 |
| Second reaction liquid (Example 2) | 13.8 |
|  | Yield of 5-(o-tolyl)pentene-(2) (%) |
| First reaction (Control 2) | 82 |
| Second reaction (Example 2) | 89 |

EXAMPLES 3 – 5 AND CONTROL 3 – 5

The experiments were carried out under identical conditions as in Example 2 and Control 2, except that as starting materials m-xylene, p-xylene and ethylbenzene were used instead of o-xylene. The results obtained are shown in Table 1.

Table 1

| Class of Starting Alkyl-benzene | Class of Intended Product | Yield of Intended Product | | | |
|---|---|---|---|---|---|
| | | Second Reaction | | First Reaction | |
| | | Experiment No. | Yield (%) | Experiment No. | Yield (%) |
| m-xylene | 5-(m-tolyl)pentene-(2) | Example 3 | 80 | Control 3 | 85 |
| p-xylene | 5-(p-tolyl)pentene-(2) | Example 4 | 80 | Control 4 | 86 |
| ethyl-benzene | 2-phenylhexene-(2) | Example 5 | 78 | Control 5 | 83 |

EXAMPLE 6

A continuous reaction apparatus consisting of five jacketed, stirrer-equipped 20-liter reaction tanks (effective liquid filling capacity of 12 liters) connected in series by means of overflow pipes whereby the reaction liquid flows from the first tank to the second tank by way of the overflow pipe and in similar manner successively to the fifth tank from which the reaction liquid is withdrawn was used, and to the first tank of this apparatus was fed o-xylene that was separated and recovered by distillation from the alkenylation reaction liquid obtained in this experiment, the o-xylene being fed at the rate of 19 kg per hour after preheating it up to 130° C. with a preheater. After adjusting the stirrers of the several tanks to rotate at 200 rpm and the inside temperature at 140° C., an alloy of metallic sodium and metallic potassium of weight ratio of sodium to potassium of 1:1 was fed to the first tank at the rate of 10 grams per hour. After 4 hours had elapsed from the time the feeding of the o-xylene and catalyst was started, 1,3-butadiene dehydrated by adsorption with molecular sieve 3A was continuously introduced to each tank at the rate of 0.22 kg per tank (at a total for the five tanks of 1.10 kg per hour) to carry out the reaction of o-xylene and 1,3-butadiene.

On the other hand, fresh o-xylene in an amount corresponding to that consumed in the reaction, after dehydration with molecular sieves type 4A until its water content was 3.3 ppm was mixed and contacted at a rate of 2.15 kg per hour with the reaction product overflowing from the fifth tank in a stirrer-equipped 3-liter mixing tank.

The resulting liquid mixture was introduced into a decanter, and the catalyst used in the reaction was separated. The hydrocarbon liquid phase obtained after separation of the catalyst was then continuously distilled in an atmospheric pressure distillation column to separate o-xylene and a component containing alkenylbenzenes as the key component. The recovered unreacted o-xylene was recycled for reuse in the above-described alkenylation reaction. On the other hand, the component containing as its key component alkenylbenzenes was submitted to further distillation under reduced pressure to obtain from the top of the column continuously at the rate of 2.82 kg per hour the intended monoalkenylbenzenes, 5-(o-tolyl)pentene-(1) and 5-(o-tolyl)pentene-(2), of 99.8% purity.

This operation was continuously operated for one month, with the result that the yield of the intended monoalkenylbenzenes was 88%.

CONTROL 6

Example 6 was repeated, except that instead of mixing and contacting the freshly fed o-xylene with the reaction product overflowing from the fifth tank it was directly contacted with the unreacted o-xylene that was recovered at the distillation column and then fed to the first tank of the reactor. The operation was continued for about a month in this manner, with the result that the yield of the intended monoalkylbezenes was 75%.

EXAMPLE 7

Example 6 was repeated, except that instead of contacting the freshly fed alkylbenzene with the reaction product overflowing from the fifth tank was conveyed to a catalyst separator where the catalyst used in the reaction was separated and the so separated catalyst was mixed with the freshly fed alkylbenzene. The resulting mixture was then conveyed to another catalyst separator where the catalyst and alkylbenzene phases were separated, following which the latter was fed to the first tank of the reactor. The operator was otherwise carried out as in Example 6 and under identical conditions as indicated therein. The reaction was operated continuously for about a month in this manner, with the result that the average yield of the intended monoalkenylbenzenes was 86%.

We claim:

1. In a process for the production of alkenylbenzene by the reaction of alkylbenzene with 1,3-butadiene in the presence of an alkali-metal catalyst in a reaction zone to form a reaction product containing alkenylbenzene, butadiene dimer, and alkali-metal catalyst, and separating this mixture in additional zones to provide said alkenylbenzene, the improvement which comprises first contacting fresh alkylbenzene feed stock with said reaction product of said reaction zone after it has left said zone to remove essentially all water and oxygen present in said alkylbenzene, separating said water-free and oxygen-free alkylbenzene from said reaction product, butadiene dimers, and said alkali-metal catalyst, and passing said water-free, dimer-free, and catalyst-free alkylbenzene to said reaction zone.

2. Process according to claim 1 wherein in the improvement the catalyst has in addition been separated from the reaction mass which was removed from the reaction zone.

3. Process according to claim 1 wherein said contacting is at a temperature between room temperature and 250° C.

4. Process according to claim 1 wherein the amount of the first-mentioned alkali metal catalyst is 0.0005–0.4 parts per 100 parts of fresh alkylbenzene.

* * * * *